United States Patent
Ueda et al.

(10) Patent No.: US 8,657,707 B2
(45) Date of Patent: Feb. 25, 2014

(54) SWING ANALYSIS METHOD

(75) Inventors: Masahiko Ueda, Kobe (JP); Kajiro Watanabe, Koganei (JP)

(73) Assignees: Dunlop Sports Co. Ltd., Kobe (JP); Sumitomo Rubber Industries, Ltd., Kobe (JP)

( * ) Notice: Subject to any disclaimer, the term of this patent is extended or adjusted under 35 U.S.C. 154(b) by 0 days.

(21) Appl. No.: 13/606,395

(22) Filed: Sep. 7, 2012

(65) Prior Publication Data

US 2013/0065711 A1    Mar. 14, 2013

(30) Foreign Application Priority Data

Sep. 9, 2011    (JP) ................... 2011-196727

(51) Int. Cl.
*A63B 69/36*    (2006.01)
(52) U.S. Cl.
USPC .......................................... 473/409; 473/212
(58) Field of Classification Search
USPC ......... 473/131, 151–152, 156, 192, 198, 199, 473/212, 213, 219–223, 409
See application file for complete search history.

(56) References Cited

U.S. PATENT DOCUMENTS

| | | | | |
|---|---|---|---|---|
| 3,717,857 A | * | 2/1973 | Evans ...................... | 340/870.13 |
| 3,945,646 A | * | 3/1976 | Hammond ................. | 473/223 |
| 5,233,544 A | * | 8/1993 | Kobayashi .................. | 702/141 |
| 5,688,183 A | * | 11/1997 | Sabatino et al. ............. | 473/212 |
| 2002/0077189 A1 | * | 6/2002 | Tuer et al. ..................... | 473/151 |
| 2002/0160848 A1 | * | 10/2002 | Burke .......................... | 473/233 |
| 2005/0261073 A1 | * | 11/2005 | Farrington et al. ........... | 473/221 |
| 2005/0288119 A1 | * | 12/2005 | Wang et al. .................... | 473/223 |
| 2006/0025229 A1 | * | 2/2006 | Mahajan et al. .............. | 473/131 |
| 2007/0010341 A1 | * | 1/2007 | Miettinen et al. ............. | 473/131 |
| 2011/0028248 A1 | * | 2/2011 | Ueda ............................ | 473/409 |
| 2011/0221012 A1 | * | 9/2011 | Bu et al. ........................ | 257/411 |

FOREIGN PATENT DOCUMENTS

| | | |
|---|---|---|
| JP | 2006-230466 A | 9/2006 |
| JP | 4145618 B2 | 9/2008 |
| JP | 2009-18043 A | 1/2009 |

* cited by examiner

*Primary Examiner* — Nini Legesse

(74) *Attorney, Agent, or Firm* — Birch, Stewart, Kolasch & Birch, LLP

(57) ABSTRACT

An analysis method includes the steps of: measuring a swing of a golf club to which a sensor capable of measuring accelerations in directions of three axes and angular velocities or angles about the three axes is attached; obtaining an index for classifying the swing based on a measuring result of the sensor; and classifying the swing based on the index. The index includes the item (a) or (b): (a) a grip angular velocity at least at one time during a downswing; and (b) a grip velocity at least at one time during the downswing. Preferably, times of an address, a top, and an impact are determined in the analysis method.

10 Claims, 22 Drawing Sheets

$$\begin{bmatrix} a & b & c \\ d & e & f \\ g & h & i \end{bmatrix}$$

*FIG. 10*

$$\begin{pmatrix} \cos\phi\cos\theta\cos\psi - \sin\phi\sin\psi & -\sin\phi\cos\psi - \cos\phi\cos\theta\sin\psi & \cos\phi\sin\theta \\ \sin\phi\cos\theta\cos\psi + \cos\phi\sin\psi & \cos\phi\cos\psi - \sin\phi\cos\theta\sin\psi & \sin\phi\sin\theta \\ -\sin\theta\cos\psi & \sin\theta\sin\psi & \cos\theta \end{pmatrix}$$

FIG. 11

$$T_1 = \begin{bmatrix} 1 & -\theta_{z1} & \theta_{y1} \\ \theta_{z1} & 1 & -\theta_{x1} \\ -\theta_{y1} & \theta_{x1} & 1 \end{bmatrix}$$

FIG. 15

$$T_2 = \begin{bmatrix} 1 & -\theta_{z2} & \theta_{y2} \\ \theta_{z2} & 1 & -\theta_{x2} \\ -\theta_{y2} & \theta_{x2} & 1 \end{bmatrix}$$

*FIG. 16*

SWING ANALYSIS METHOD

The present application claims priority on Patent Application No. 2011-196727 filed in JAPAN on Sep. 9, 2011, the entire contents of which are hereby incorporated by reference.

BACKGROUND OF THE INVENTION

1. Field of the Invention

The present invention relates to an analysis method of a golf swing.

2. Description of the Related Art

A golf swing differs for every golfer. A golf club influences a swing. The matching of the golfer with the golf club is important. The matching the swing with a golf ball is important. Suitable swing analysis enables precise fitting.

The swing analysis is essential for the development of a golf club and a golf ball or the like. The result of the swing analysis can be the basis of the selection of the golf club and the golf ball. The swing analysis is useful for sales promotion of the golf club and the golf ball or the like.

In Japanese Patent Application Laid-Open No. 2006-230466, a swing is evaluated by measurement using a magnetic sensor. In Japanese Patent Application Laid-Open No. 2009-18043, a swing is evaluated by using an image. In Japanese Patent Application Publication No. 4145618, a shaft is selected based on measurement using a strain gauge.

SUMMARY OF THE INVENTION

The measuring devices described in the literatures are large-sized and complicated. The measuring devices are unsuitable for hardware for fitting in stores. Although a motion capture system is also put to practical use, the motion capture system is expensive. On the other hand, if a swing which is a complicated operation can be appropriately classified, the fitting is facilitated and precise.

It is an object of the present invention to provide a swing analysis method capable of classifying a swing using a simple device.

A swing analysis method according to the present invention includes the steps of: measuring a swing of a golf club to which a sensor capable of measuring accelerations in directions of three axes and angular velocities or angles about the three axes is attached; obtaining an index for classifying the swing based on a measuring result of the sensor; and classifying the swing based on the index. The index includes the following item (a) or (b):

(a) a grip angular velocity at least at one time during a downswing; and (b) a grip velocity at least at one time during the downswing.

Preferably, times of an address, a top, and an impact are determined in the analysis method.

Preferably, the index includes at least two selected from the following items (c), (d), and (e):

(c) a grip angular velocity in a toe-down direction;

(d) a grip angular velocity about a shaft axis; and (e) a grip velocity in a direction toward a golfer.

According to another preferred aspect, the index includes at least two selected from the following items (c), (d), and (f):

(c) a grip angular velocity in a toe-down direction;

(d) a grip angular velocity about a shaft axis; and (f) a dynamic loft angle of a head.

According to another preferred aspect, the index includes at least two selected from the following items (c), (d), and (g):

(c) a grip angular velocity in a toe-down direction;

(d) a grip angular velocity about a shaft axis; and (g) a grip attitude angle at an impact.

A fitting method according to the present invention is a method for fitting a golf club using any of the swing analysis methods. In the fitting method, a recommended shaft is defined for each swing classification.

In the swing analysis method, the swing can be classified by a simple device.

BRIEF DESCRIPTION OF THE DRAWINGS

FIG. 10 shows an example of attitude matrices;

FIG. 11 shows an Euler transformation matrix;

FIG. 15 shows an example of rotation matrices;

FIG. 16 shows another example of the rotation matrices;

DESCRIPTION OF THE PREFERRED EMBODIMENTS

Hereinafter, the present invention will be described in detail based on the preferred embodiments with appropriate references to the accompanying drawings.

Figure 1:
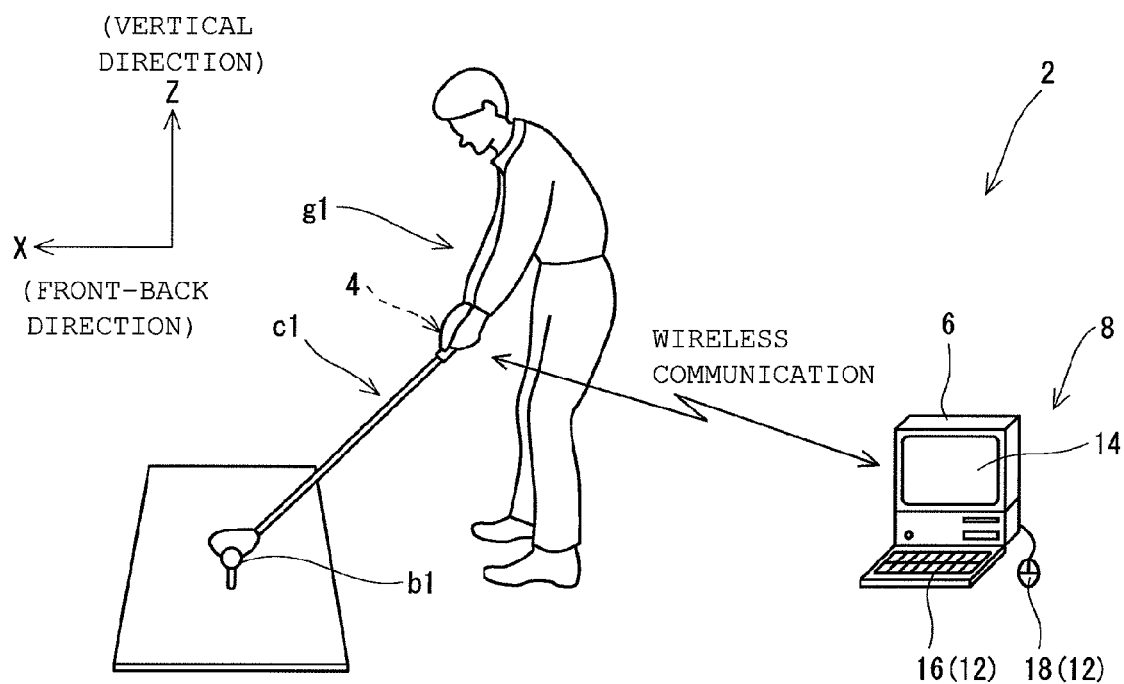
FIG. 1 shows an example of swing measurements according to the present invention.

As shown in FIG. 1, a swing analysis system 2 is used in the embodiment.

The swing analysis system 2 is provided with a sensor 4, a wireless receiving device 6 incorporated in a computer, and a data analysis device 8. In FIG. 1, the sensor 4 is hidden by arms of a golfer g1.

Figure 2:
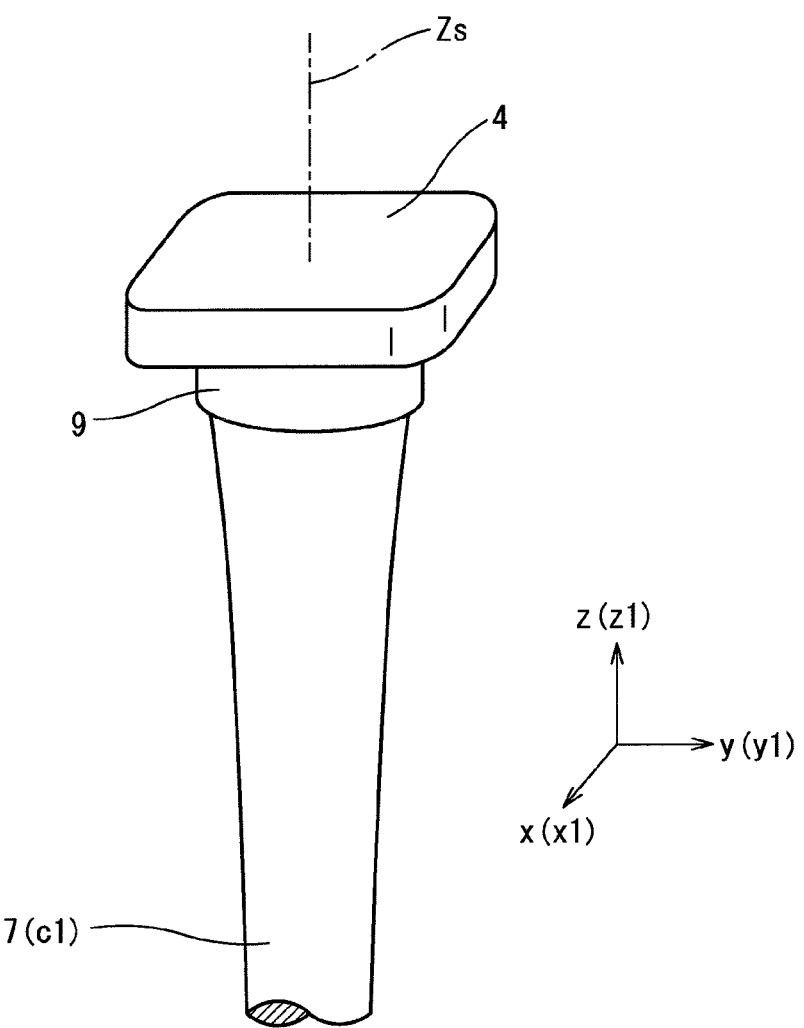
FIG. 2 is an enlarged perspective view of a golf club to which a sensor is attached.
Figure 3A:
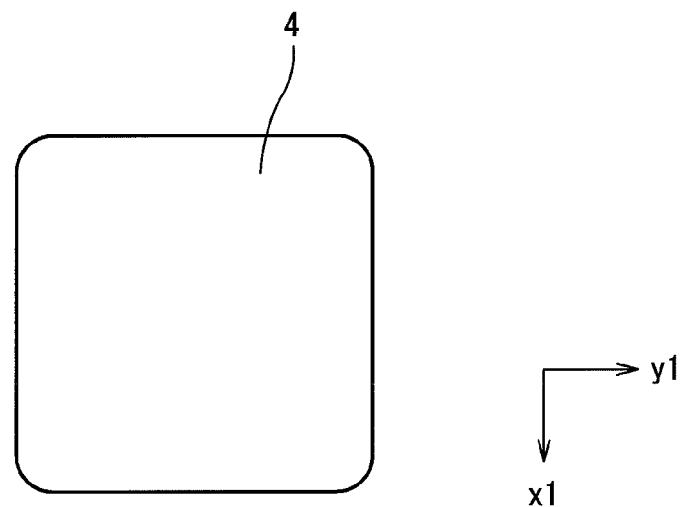
FIG. 3A is a plan view of the sensor.
Figure 3B:
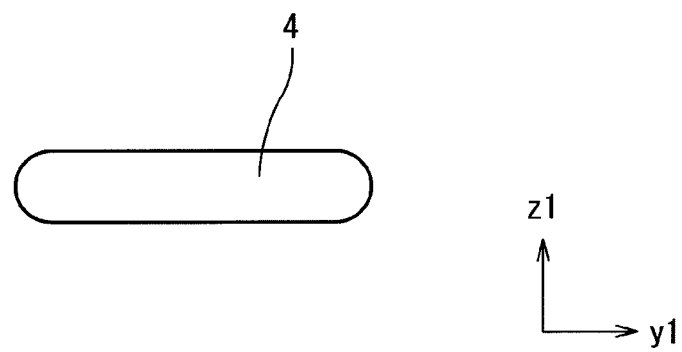
FIG. 3B is a side view of the sensor.

FIG. 2 is a perspective view showing the sensor 4 attached to a grip end of a golf club c1. FIG. 3A is a plan view of the sensor 4. FIG. 3B is a front view of the sensor 4. The sensor 4 is attached to a back end of a grip 7. The sensor 4 is attached to the grip 7 with an adapter 9 sandwiched between the sensor 4 and the grip 7. The sensor 4 is easily attached by a double-face tape, an adhesive, and screwing or the like. The sensor 4 is compact and lightweight.

The sensor 4 is a wireless type. The sensor 4 can transmit measured data by wireless. The details for wireless communication will be described later. The specification and technique of, for example, Bluetooth can be suitably used as the wireless communication.

The sensor 4 includes an acceleration sensor capable of measuring acceleration in each of directions of three axes (x1 axis, y1 axis, and z1 axis). The sensor 4 includes an angular velocity sensor capable of measuring angular velocities about the directions of the three axes (x1 axis, y1 axis, and z1 axis). Furthermore, the sensor 4 is provided with an A/D converter, a CPU, a wireless interface, a wireless antenna, and a power source. A battery is used as the power source. For example, a compact battery such as a lithium-ion battery is suitably used as the battery. A so-called button type battery can be suitably used. The battery may be chargeable. The sensor 4 may be provided with a charge circuit for charging the battery. Examples of the sensor 4 include "WAA-010" (trade name) manufactured by Wireless Technologies, Inc.

An angle sensor may be used in place of the angular velocity sensor. That is, a sensor capable of measuring angles about the three axes may be used.

Although not shown in the drawings, the wireless receiving device 6 is provided with a wireless antenna, a wireless interface, a CPU, and a network interface.

For example, a computer is used as the data analysis device 8. The data analysis device 8 is provided with an input part 12 and a display part 14. Although not shown in the drawings, the data analysis device 8 is provided with a hard disk, a memory, a CPU, and a network interface. The input part 12 has a keyboard 16 and a mouse 18.

FIG. 1 shows the golfer g1, the golf club c1, and a golf ball b1 besides the swing analysis system 2. The golfer g1 drawn in FIG. 1 is in an address state. The golfer g1 is a right-handed person.

The sensor 4 detects acceleration in a direction of each of the x1 axis, the y1 axis, and the z1 axis. As shown in FIG. 2, the x1 axis, the y1 axis, and the z1 axis constitute a three-axis orthogonal coordinate system. These accelerations are obtained as an analog signal. The analog signal is converted into a digital signal by the A/D converter. Output from the A/D converter is transmitted to, for example, the CPU, to execute calculation processing such as primary filtering. In this way, data processed in the sensor 4 is transmitted from the wireless antenna via the wireless interface.

The sensor 4 detects angular velocity about each of the x1 axis, the y1 axis, and the z1 axis. These angular velocities are obtained as an analog signal. The analog signal is converted into a digital signal by the A/D converter. Output from the A/D converter is transmitted to, for example, the CPU, to execute calculation processing such as primary filtering. In this way, data processed in the sensor 4 is transmitted from the wireless antenna via the wireless interface.

The data transmitted from the wireless antenna of the sensor 4 is received by the wireless interface via the wireless antenna of the wireless receiving device 6 side. The received data is subjected to calculation processing by, for example, the CPU, and is sent to the data analysis device 8.

The data sent to the data analysis device 8 is recorded in a memory resource such as a hard disk. The hard disk stores a program and data or the like required for data processing or the like. The program causes the CPU to execute necessary data processing. The CPU can execute various calculation processings. An example of the calculation processing will be described later. The calculation result is output by the display part 14, or a printer which is not shown, or the like.

A relation between a measurement axis and the golf club is considered in attachment of the sensor 4. In the embodiment, the z1 axis of the sensor 4 is coincident with a shaft axis Zs of the golf club c1. The x1 axis of the sensor 4 is aligned so as to be along a toe-heel direction of a head as much as possible. The y1 axis of the sensor 4 is aligned so as to be along a normal direction of a face surface as much as possible. In this way, the calculation is simplified by attaching the sensor 4.

[Whole Coordinate System and Local Coordinate System]

In the present application, a whole coordinate system and a local coordinate system are considered. For the convenience of the description, the axes of the whole coordinate system are represented by an X axis, a Y axis, and a Z axis. The axes of the local coordinate system are represented by an x axis, a y axis, and a z axis.

The X axis, the Y axis, and the Z axis of the whole coordinate system are a three-dimensional orthogonal coordinate system. In order to facilitate analysis, in the embodiment, the Z axis is set in a vertical direction, and the X axis is set in a front-back direction of the golfer g1. The Y axis is set in a target direction. In more detail, the Y axis connects a hitting ball point and a target point, and is set in a direction parallel to a ground.

The x axis, the y axis, and the z axis of the local coordinate system are a three-dimensional orthogonal coordinate system. In order to facilitate analysis, in the embodiment, the z axis is defined as the shaft axis Zs. The x axis is set so as to be along the toe-heel direction of the head as much as possible. The y axis is set so as to be along the normal direction of the face surface as much as possible.

The z axis of the local coordinate system is coincident with the z1 axis of the sensor 4. The y axis of the local coordinate system is coincident with the y1 axis of the sensor 4. The x axis of the local coordinate system is coincident with the x1 axis of the sensor 4. The following six data are directly obtained as measured values by the setting.

The data directly obtained as the measured values of the sensor 4 are the following six data.

an angular velocity $\omega x$ about an x axis (grip angular velocity $\omega x$)

an angular velocity $\omega y$ about a y axis (grip angular velocity $\omega y$)

an angular velocity $\omega z$ about a Z axis (grip angular velocity $\omega z$)

acceleration Ax in an x axis direction acceleration Ay in a y axis direction acceleration Az in a z axis direction A plurality of data which are continuous in time-series are obtained by the sensor 4. The number of data per a unit period depends on a sampling frequency.

In the golfer g1 in the address state, the Y axis of the whole coordinate system and the y axis of the local coordinate system are substantially parallel to each other. The directions of the local coordinate system to the whole coordinate system is changed from moment to moment during a swing. The direction of the local coordinate system is changed in association with the motion of the golf club c1.

Figure 4:
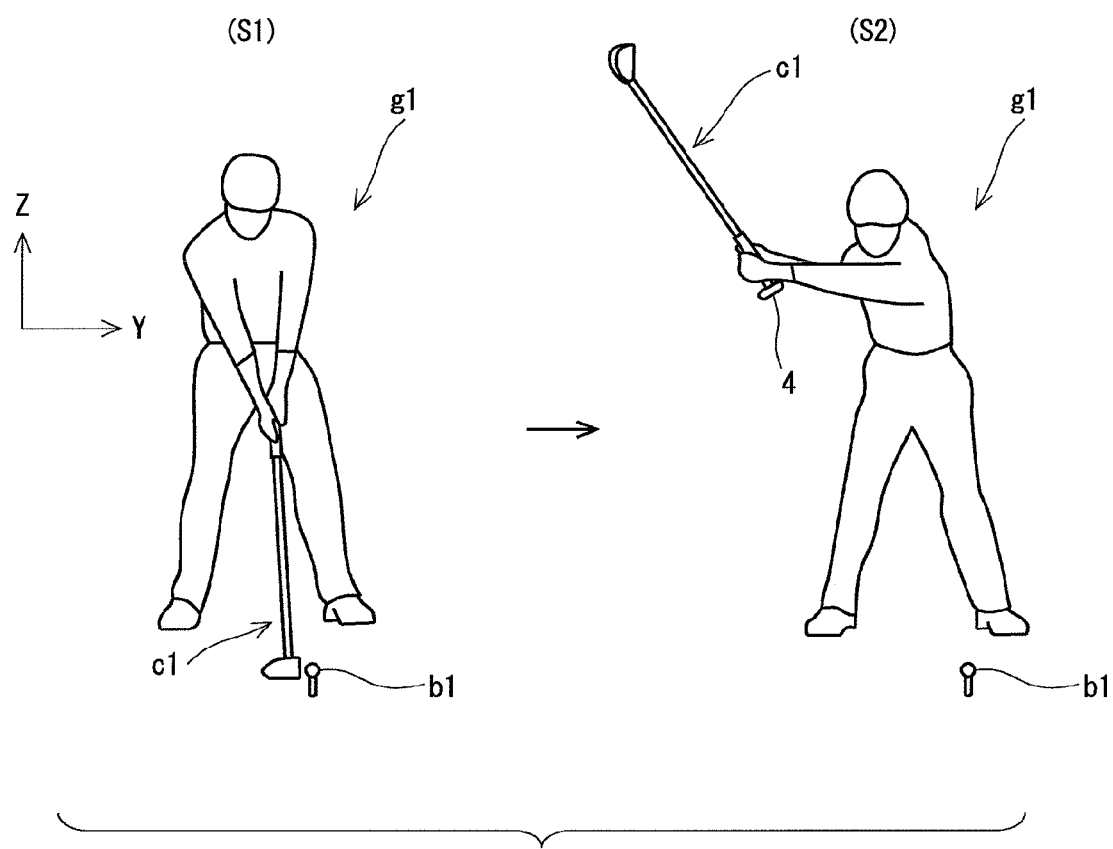
FIG. 4 shows a aspect of a swing, and shows an address and a back-swing.
Figure 5:
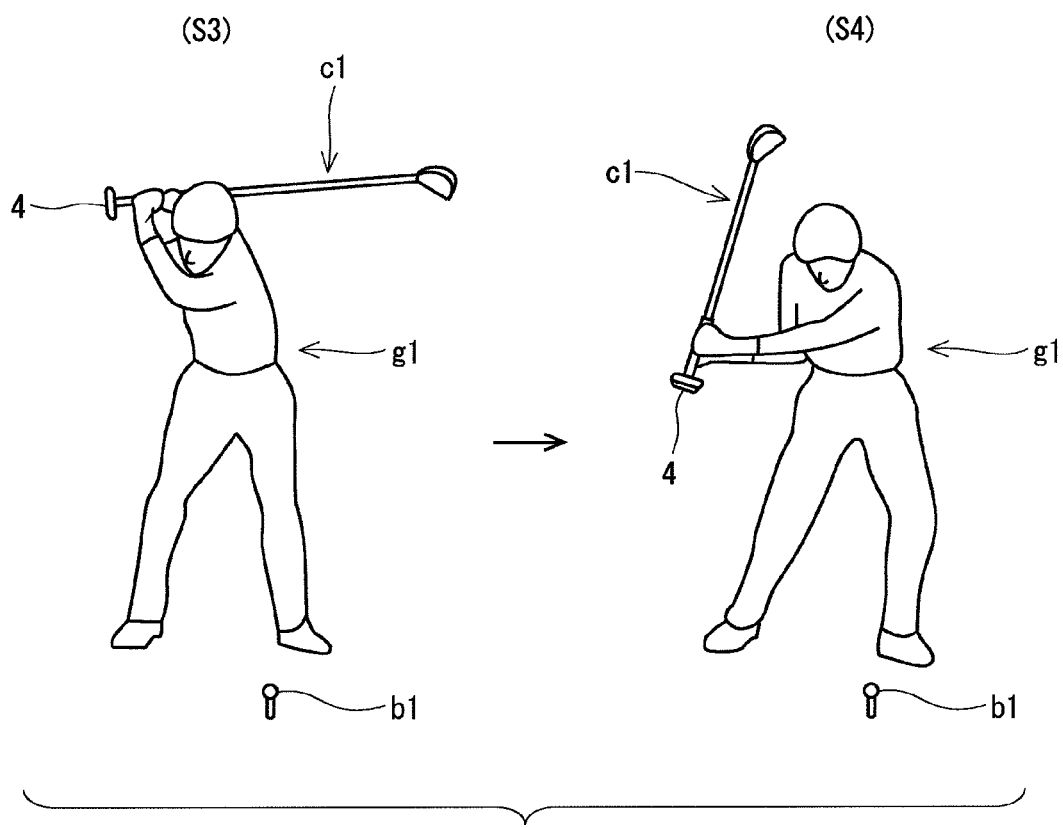
FIG. 5 shows a aspect of a swing, and shows a top and a downswing.
Figure 6:
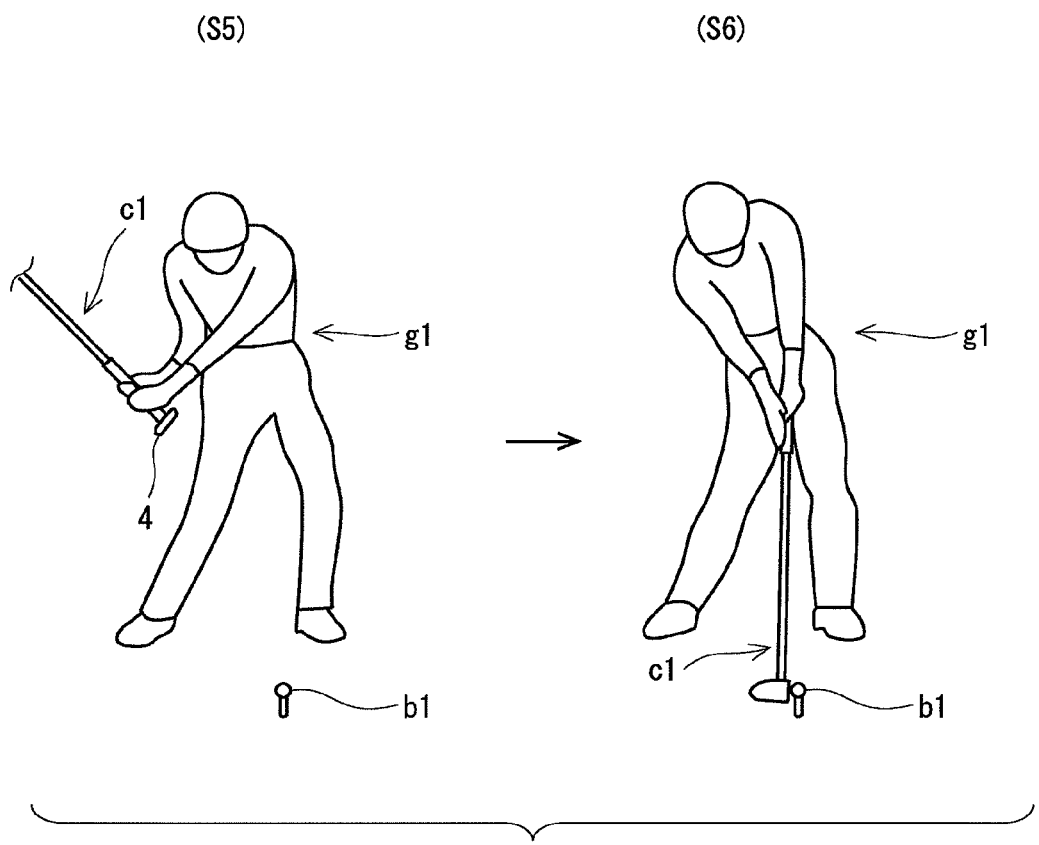
FIG. 6 shows a aspect of a swing, and shows a downswing and an impact.
Figure 7:
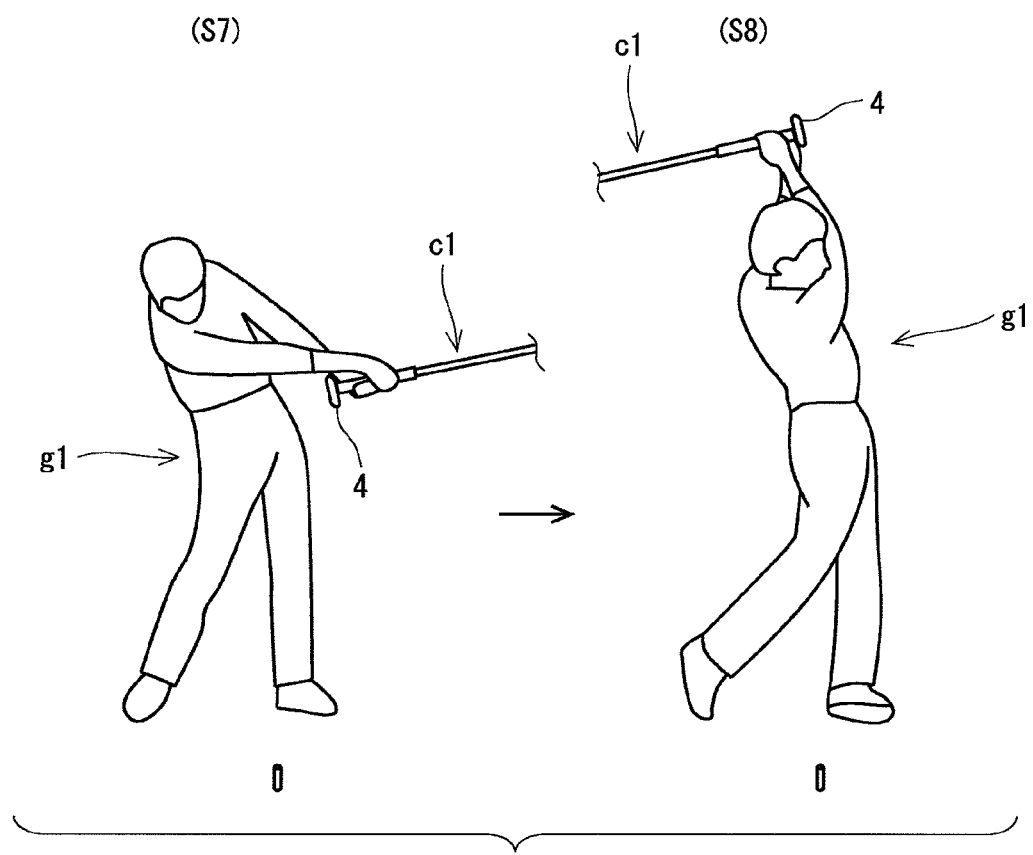
FIG. 7 shows a aspect of a swing, and shows a follow-through and a finish.

FIGS. 4 to 7 describe the swing. FIGS. 4 to 7 are views of the golfer g1, as viewed from the front face (front side) of the golfer g1. The start of the swing is an address. The end of the swing is referred to as a finish. The swing progresses in order of (S1), (S2), (S3), (S4), (S5), (S6), (S7), and (S8). (S1) and (S2) are shown in FIG. 4. (S3) and (S4) are shown in FIG. 5. (S5) and (S6) are shown in FIG. 6. (S7) and (S8) are shown in FIG. 7. (S1) of FIG. 4 is an address. (S2) of FIG. 4 is a back-swing. (S3) of FIG. 5 is a top (top of swing). Usually, in the top of swing, the movement velocity of the head during the swing is the minimum. (S4) of FIG. 5 is a downswing. (S5) of FIG. 6 is also a downswing. (S5) is in a state where the downswing progresses from (S4). (S6) of FIG. 6 is an impact. The impact is a moment when the head of the golf club c1 and the golf ball b1 collide with each other. (S7) of FIG. 7 is a follow-through. (S8) of FIG. 7 is a finish. The swing is ended at the finish.

A step of searching an index for classifying the swing is performed as preparation for using the swing analysis system 2. A motion capture system is used in the search of the index. In the search of the index, the swings of 20 golfers are analyzed, and 43 kinds of swing features are quantified. Separately, each of the 20 golfers tries five clubs, to obtain evaluation data for a flight distance, suppression of curving of a hit ball, and easiness to swing. Statistical analysis is performed based on the 43 kinds of swing features and the evaluation data. A technique referred to as discrimination analysis is used in the statistical analysis. As a result, it is found that some of the 43 kinds of swing features are effective as the index for classifying the swing. Particularly, knowledge that the following three indices are statistically effective for 70% or more of the golfers is obtained:

(index 1) angular velocity in a toe-down direction during a downswing;

(index 2) angular velocity about a shaft axis Zs during the downswing; and (index 3) a grip velocity in a direction toward a golfer near an impact (preferably, at the impact).

The angular velocity of the index 1 corresponds to the angular velocity about the y axis. Therefore, the angular velocity is expressed as $\omega y$ in the present application. The angular velocity of the index 2 corresponds to the angular velocity about the z axis. Therefore, the angular velocity is expressed as $\omega z$ in the present application.

A system for easily measuring these effective indices is considered, and the swing analysis system 2 is obtained. In the swing analysis method, swing analysis is enabled by only data from the sensor 4.

The swing analysis method using the swing analysis system 2 includes the following steps st1 to st3.

the step st1 of swinging the golf club c1 to which the sensor 4 capable of measuring accelerations in directions of three axes and angular velocities about the three axes is attached;

the step st2 of obtaining an index for classifying the swing based on a measuring result of the sensor; and the step st3 of classifying the swing based on the index.

The index includes the following item (a) or (b):

(a) a grip angular velocity at least at one time during a downswing; and (b) a grip velocity at least at one time during the downswing.

The term "during a downswing" is a period between an address and an impact.

Preferably, in the swing analysis method, the times of the address, the top, and the impact are determined based on the measuring result of the sensor. These times are grasped, and thereby the times at which the data should be acquired can be easily grasped.

Preferably, the index includes at least two selected from the following items (c), (d), and (e). More preferably, the index includes all of the following items (c), (d), and (e):

(c) a grip angular velocity $\omega y$ in a toe-down direction;

(d) a grip angular velocity $\omega z$ about a shaft axis; and (e) a grip velocity Vx in a direction toward a golfer.

The above item (c) is a value at least at one time. The above item (c) is preferably an average value in view of improving accuracy for classifying the swing. The average value is obtained by averaging measured values between a time t1 and a time t2. The times t1 and t2 are times during the downswing. The time t1 may be set to the top, and the time t2 may be set to the impact.

The above item (d) is a value at least at one time. The above item (d) is preferably an average value in view of improving the accuracy for classifying the swing. The average value is obtained by averaging measured values between a time t1 and a time t2. The times t1 and t2 are times during the downswing. The time t1 may be set to the top, and the time t2 may be set to the impact.

In view of improving the accuracy for classifying the swing, preferably, the above item (e) is a value near an impact. The term "near an impact" means a period between 0.01 second prior to the impact and the impact. More preferably, the above item (e) is a value at the impact.

The grip velocity Vx in the direction of the golfer is a velocity in a direction of the x axis. The grip velocity Vx can be an index for a change in a distance between a grip and the golfer. Some golfers perform an operation of drawing the grip in directions of their own bodies near the impact. The grip velocity Vx can be changed depending on the degree of the operation.

In place of the grip velocity Vx, other velocity capable of showing the change in the distance between the grip and the golfer may be employed.

Figure 8:
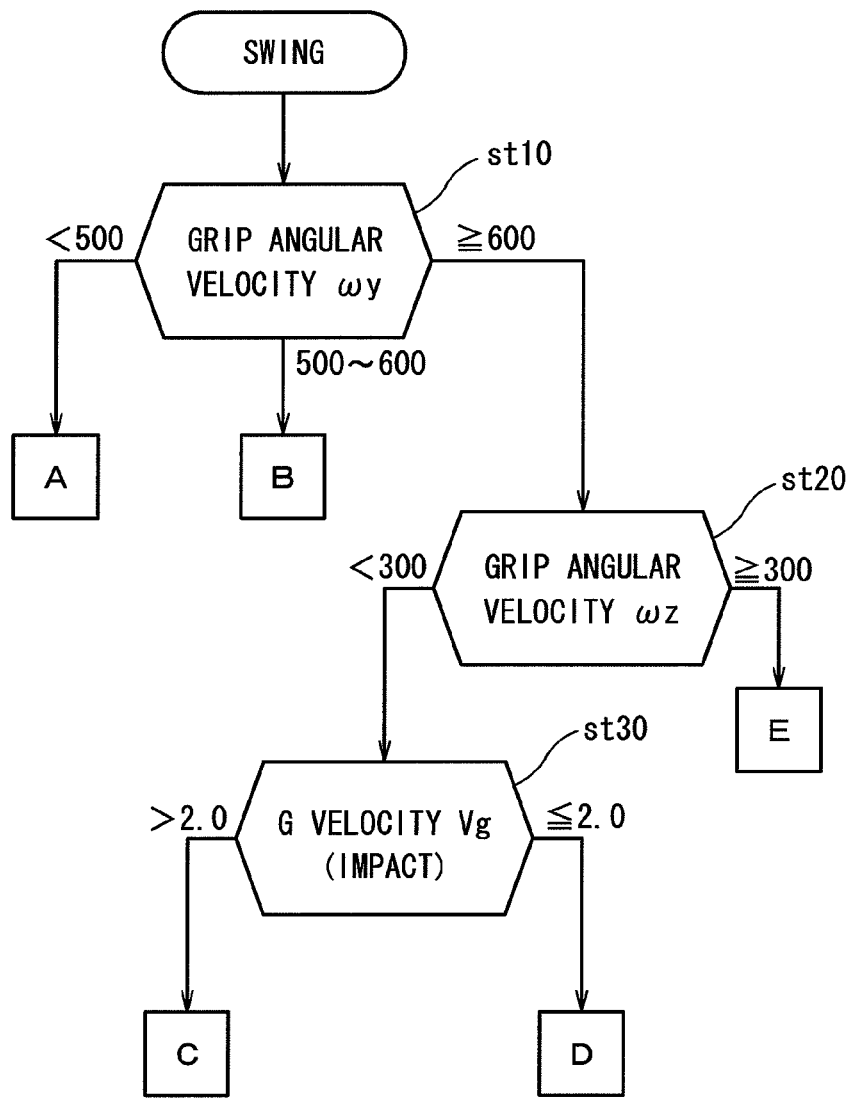
FIG. 8 is a flow chart showing an example of the steps of classifying a swing.

FIG. 8 is a flow chart showing a swing classifying step st3 using the above items (c), (d), and (e). In the swing classification, the grip angular velocity $\omega y$ of the above item (c) is determined (step st10). When the grip angular velocity $\omega y$ is less than 500 (deg/s), the swing is classified into a swing pattern A. When the grip angular velocity $\omega y$ is 500 (deg/s) or greater and less than 600 (deg/s), the swing is classified into a swing pattern B. When the grip angular velocity $\omega y$ is equal to or greater than 600 (deg/s), the processing proceeds to the following step st20. Values other than 500 (deg/s) and 600 (deg/s) may be used. That is, a threshold value can be suitably set. In the embodiment, the average value in the overall downswing is employed as the grip angular velocity $\omega y$.

Next, the grip angular velocity $\omega z$ of the above item (d) is determined (step st20). When the grip angular velocity $\omega z$ is equal to or greater than 300 (deg/s), the swing is classified into a swing pattern E. When the grip angular velocity $\omega z$ is less than 300 (deg/s), the processing proceeds to the following step st30. Values other than 300 (deg/s) may be used. That is, a threshold value can be suitably set. In the embodiment, the average value in the overall downswing is employed as the grip angular velocity $\omega z$.

Next, the grip velocity Vx of the above item (e) is determined (step st30). When the grip velocity Vx is less than 2.0 (m/s), the swing is classified into a swing pattern C. When the grip velocity Vx is equal to or greater than 2.0 (m/s), the swing is classified into a swing pattern D. Values other than 2.0 (m/s) may be used. That is, a threshold value can be suitably set. In the embodiment, the value at the impact is employed as the grip velocity Vx.

As described above, the swing can be classified into the five patterns A to E.

In another preferred aspect, the index includes at least two selected from the following items (c), (d), and (f). More preferably, the index includes all of the following items (c), (d), and (f):

(c) a grip angular velocity $\omega y$ in a toe-down direction;

(d) a grip angular velocity $\omega z$ about a shaft axis; and (f) a dynamic loft angle DL of a head.

The dynamic loft angle DL is an inclination angle of the face surface to the vertical direction. In view of improving the accuracy for classifying the swing, the above item (f) is preferably a value near the impact, and more preferably a value at the impact. The dynamic loft angle DL is measured based on a head image near the impact, for example.

Figure 9:
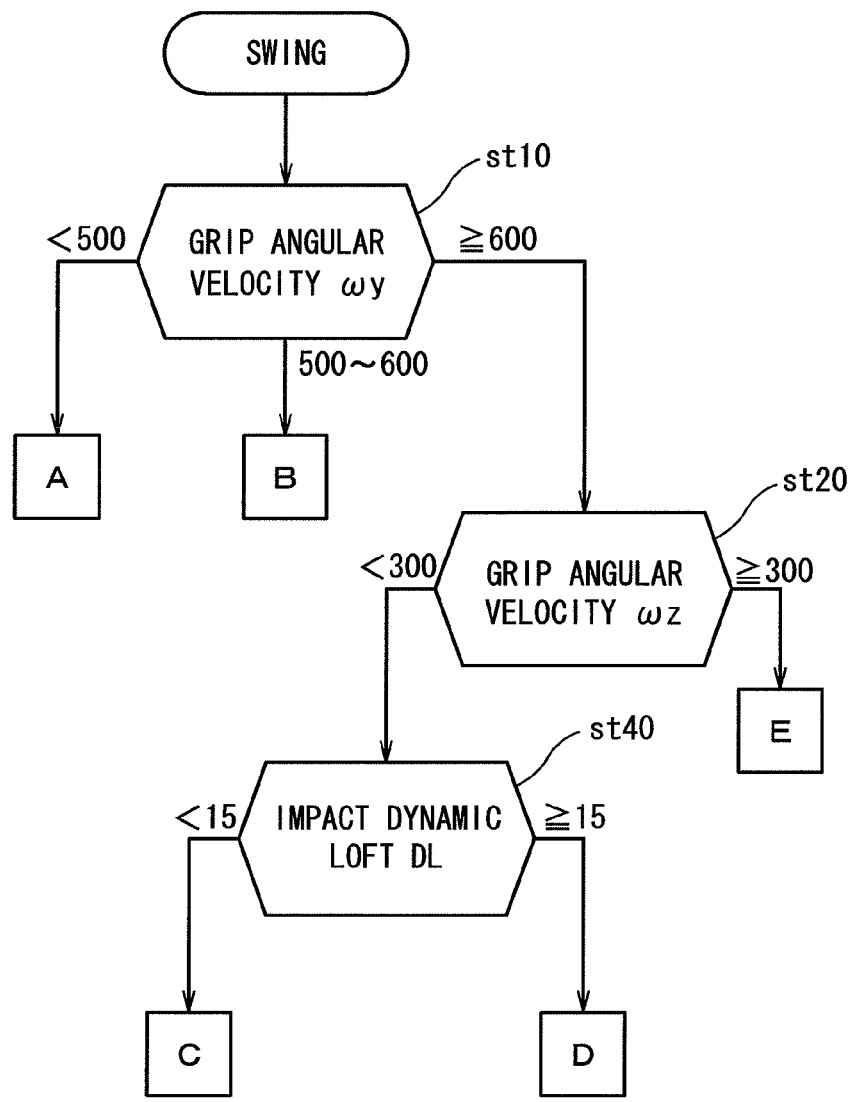
FIG. 9 is a flow chart showing another example of the steps classifying a swing.

FIG. 9 is a flow chart showing the swing classifying step st3 using the above items (c), (d), and (f). The step st10 and the step st20 are the same as those of the embodiment of FIG. 8. In the embodiment, a step st40 is performed in place of the step st30. In the step st40, the dynamic loft angle DL at the impact is determined. When the dynamic loft angle DL is less than 15 (degrees), the swing is classified into the swing pattern C. When the dynamic loft angle DL is equal to or greater than 15 (degrees), the swing is classified into the swing pattern D. Values other than 15 (degrees) may be used. That is, a threshold value can be suitably set.

The swing analysis method is used in a fitting method according to the present invention. In the fitting method, a recommended shaft is defined for each swing classification. In the fitting method, the recommended shaft is determined by classifying the swing. Generally, it is difficult to select the shaft in the fitting. The shaft can be easily selected in the fitting method.

Next, a method for calculating each index will be described.

[Grip Angular Velocity]

The grip angular velocity can be directly obtained from the angular velocity obtained by the sensor 4. In the embodiment, the angular velocity about the y1 axis of the sensor 4 is equal to the grip angular velocity ωy. The angular velocity about the z1 axis of the sensor 4 is equal to the grip angular velocity ωz. The angular velocity about the x1 axis of the sensor 4 is equal to the angular velocity (grip angular velocity ωx) about the x axis.

[Grip Inclination Angle α]

A grip inclination angle α is determined by obtaining an attitude matrix to be described later. A method for calculating the angle α from the attitude matrix will be described later. The angle α is an angle between the Y axis and the shaft axis line, as viewed from the front face.

[Grip Velocity]

Usually, a velocity is obtained by integrating the acceleration. Since the accelerations in the directions of the three axes are measured by the sensor 4, it is considered to integrate the accelerations. However, the grip velocity cannot be calculated by the simple integration.

The accelerations measured by the sensor 4 include the following three accelerations:

(acceleration 1) acceleration of a translational component;
(acceleration 2) acceleration of a centrifugal component; and
(acceleration 3) gravitational acceleration.

In order to obtain the grip velocity (translational velocity), it is necessary to integrate only the acceleration of the translational component. For that purpose, it is necessary to eliminate the acceleration of the centrifugal component and the gravitational acceleration.

Figure 10:
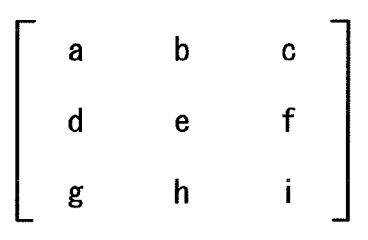

The attitude matrix is used in the calculation of the grip velocity. FIG. 10 shows the attitude matrix. The attitude matrix has nine components a to i. The attitude of the grip is described in the attitude matrix. The meaning of each component in the attitude matrix is as follows:

component a: cosine (cos) of an angle between the X axis of the whole coordinate system and the x axis of the local coordinate system;

component b: cosine (cos) of an angle between the Y axis of the whole coordinate system and the x axis of the local coordinate system;

component c: cosine (cos) of an angle between the Z axis of the whole coordinate system and the x axis of the local coordinate system;

component d: cosine (cos) of an angle between the X axis of the whole coordinate system and the y axis of the local coordinate system;

component e: cosine (cos) of an angle between the Y axis of the whole coordinate system and the y axis of the local coordinate system;

component f: cosine (cos) of an angle between the Z axis of the whole coordinate system and the y axis of the local coordinate system;

component g: cosine (cos) of an angle between the X axis of the whole coordinate system and the z axis of the local coordinate system;

component h: cosine (cos) of an angle between the Y axis of the whole coordinate system and the z axis of the local coordinate system; and component i: cosine (cos) of an angle between the Z axis of the whole coordinate system and the z axis of the local coordinate system.

The three components (a, b, c) show a direction of an x-axis vector of the local coordinate system. The three components (d, e, f) show a direction of a y-axis vector of the local coordinate system. The three components (g, h, i) show a direction of a z-axis vector of the local coordinate system.

The attitude of the grip is changed from moment to moment during the swing. Therefore, the attitude matrix is also changed from moment to moment during the swing.

In a method for calculating the grip velocity, the acceleration of the centrifugal component and the gravitational acceleration are removed, and the acceleration is then integrated. In the calculating method, the attitude matrix in the address is firstly calculated (step st100). Next, the attitude matrix at each time is calculated (step st200). Next, the measured acceleration data is converted into the whole coordinate system (step st300). The acceleration of the centrifugal component is removed by the conversion. Next, the acceleration at the address is offset (step st400). The gravitational acceleration is removed by the offset. Finally, the acceleration from which the acceleration of the centrifugal component and the gravitational acceleration are removed is integrated (step st500). The grip velocity is obtained by the integration.

The attitude matrix at the address can be calculated by utilizing the action of a gravitational force in the vertical direction in the step st100. In the step st100, the component c, the component f, and the component i of the attitude matrix are firstly obtained (step st110). Since the gravitational force acts in the vertical direction, i.e., in the direction of the Z axis of the whole coordinate system, the component c, the component f, and the component i can be directly calculated based on the acceleration data by the sensor. Next, the other six components are calculated using the component c, the component f, and the component i which are obtained (step st120). The six components can be also calculated by geometric calculation as in the components c, f, and i. Multiple linear regression analysis can be used in the calculation of the six components. An Euler transformation matrix may be used in the calculation of the six components. FIG. 11 shows the Euler transformation matrix.

In the embodiment, the component a and the component g of the six components can be presumed with high accuracy by the multiple linear regression analysis. A multiple correlation coefficient showing the accuracy of the presumption is 0.98.

On the other hand, in the other four components b, d, e, and h, high accuracy is not obtained in the presumption by the multiple linear regression analysis. The component b is presumed using the Euler transformation matrix. That is, the Euler transformation matrix is contrasted with the components a, c, f, g, and i which are known values, to obtain $\theta$, $\phi$, and $\Psi$ which are Euler angles. The component b is obtained based on these Euler angles. When the component b is compared with the component b obtained by motion capture, a correlation coefficient is 0.86.

Plus or minus of $\Psi$ of the Euler angles cannot be determined from only angle information. The plus or the minus is determined based on the calculation result of the grip angle at the address, for example. A method for calculating the grip angle will be described later.

The component h of the other components is calculated by utilizing an angle of 90 degrees between the x axis and the z axis. The components d and e are calculated by the following formulae using the values of the other components.

$$d = b \cdot i = c \cdot h$$

$$e = a \cdot i - c \cdot g$$

Figure 12:
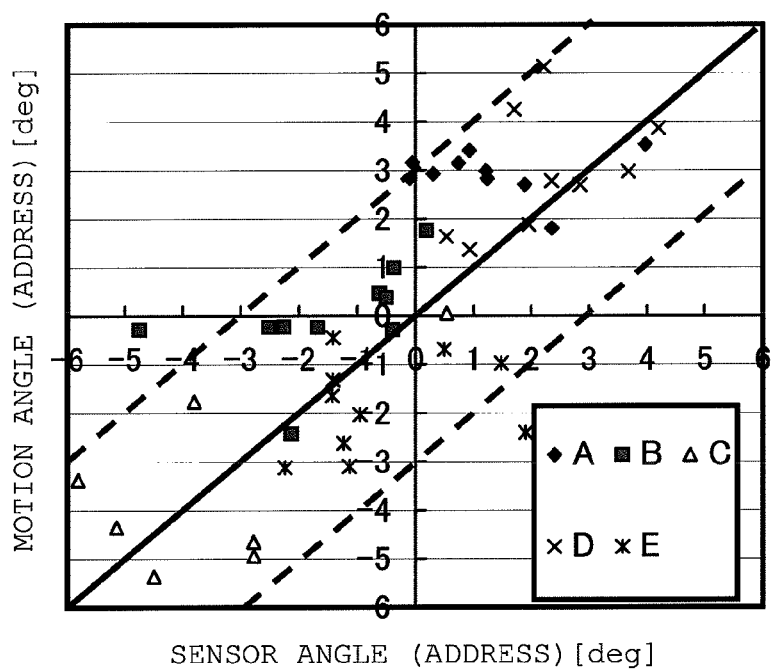
FIG. 12 is a graph showing a verification result of a calculated value of a grip attitude angle.
Figure 13:
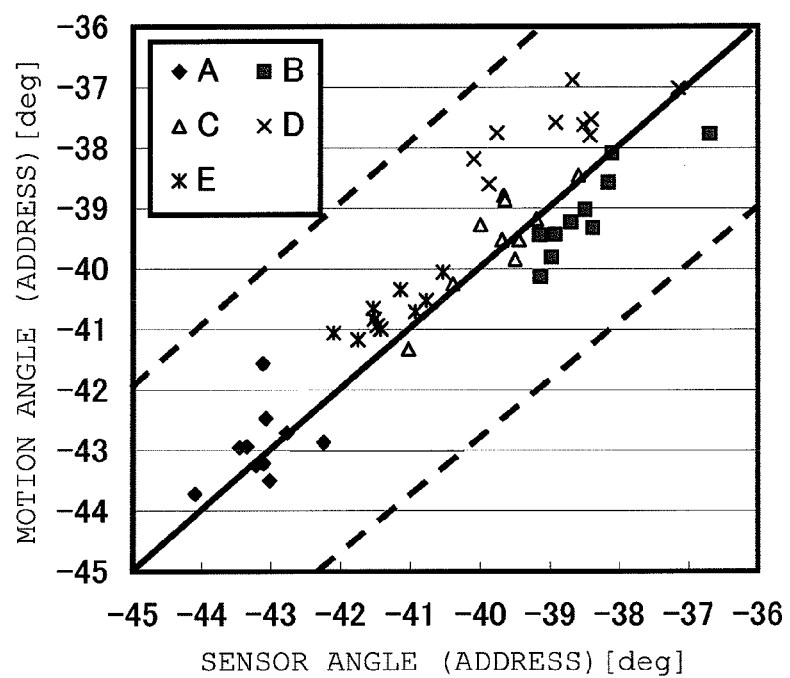
FIG. 13 is another graph showing the verification result of the calculated value of the grip attitude angle.
Figure 14:
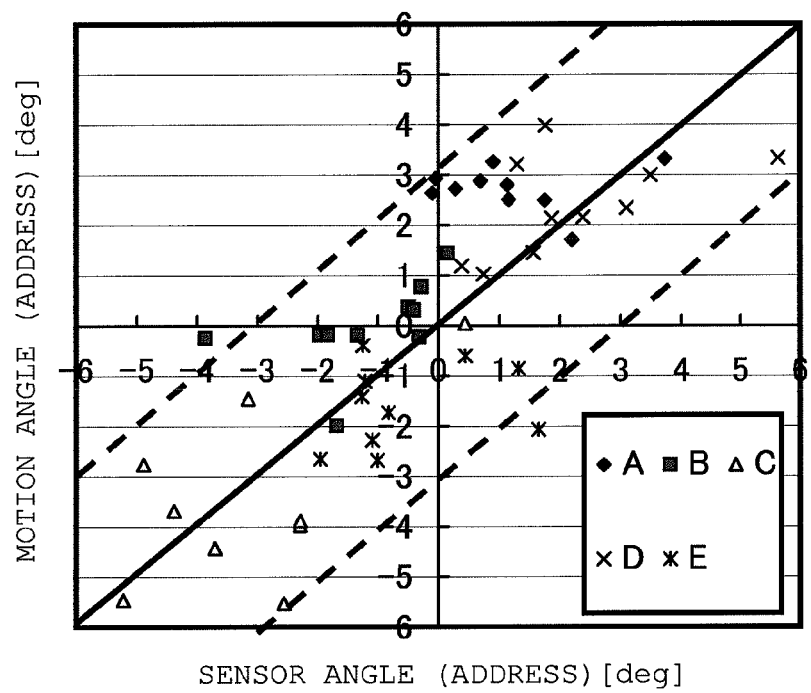
FIG. 14 is another graph showing the verification result of the calculated value of the grip attitude angle.

The accuracy of the attitude matrix calculated based on the above description is verified. The verification is performed by comparing the grip attitude of the attitude matrix with the grip attitude obtained by the motion capture. The verification is performed based on the measured data of five testers (testers A, B, C, D, and E). The results are shown in graphs of FIGS. 12 to 14. FIG. 12 is a graph related to a grip angle $\alpha$ in the address. FIG. 13 is a graph related to a grip angle $\beta$ in the address. FIG. 14 is a graph related to a grip angle $\gamma$ in the address. In FIGS. 12 to 14, a horizontal axis is an angle calculated based on the attitude matrix, and a vertical axis is an angle calculated based on the motion capture. In any of these graphs, the value of the vertical axis is substantially coincident with the value of the horizontal axis. In most data, the error is within ±3 (degrees). Therefore, it is considered that the accuracy of the attitude matrix is high. The grip angles $\alpha$, $\beta$, and $\gamma$ will be described later.

In the step st200, the product of an attitude matrix $N_1$ and a rotation matrix $T_1$ at the address is obtained (step st210). An attitude matrix $N_2$ is obtained by the product. That is, $N_2 = N_1 \cdot T_1$ is set.

FIG. 15 shows the rotation matrix $T_1$. The rotation matrix $T_1$ is determined by an angle change amount between the time of the address and a first sampling time T1. The angle change amount is the product of each of the angular velocity $\omega x1$, $\omega y1$, and $\omega z1$ of the sensor 4 at the sampling time T1 and a period $\Delta t$. The period $\Delta t$ corresponds to a unit period of measurement sampling. The period $\Delta t$ is also referred to as a sampling period. In the rotation matrix $T_1$, $\theta_{x1} = \omega x1 \cdot \Delta t$ is set; $\theta_{y1} = \omega y1 \cdot \Delta t$ is set; and $\theta_{z1} = \omega z1 \cdot \Delta t$ is set.

Next, the product of the attitude matrix $N_2$ and a rotation matrix $T_2$ is obtained (step st220). An attitude matrix $N_3$ is obtained by the product. That is, $N_3 = N_2 \cdot T_2 = N_1 \cdot T_1 \cdot T_2$ is set.

FIG. 16 shows the rotation matrix $T_2$. The rotation matrix $T_2$ is determined by an angle change amount between the sampling time T1 and a sampling time T2. The angle change amount is the product of each of angular velocities $\omega x2$, $\omega y2$, and $\omega z2$ of the sensor 4 at the sampling time T2 and a period $\Delta t$. In the rotation matrix $T_2$, $\theta_{x2} = \omega x2 \cdot \Delta t$ is set; $\theta_{y2} = \omega y2 \cdot \Delta t$ is set; and $\theta_{z2} = \omega z2 \cdot \Delta t$ is set.

Hereinafter, the product of an attitude matrix $N_i$ and a rotation matrix $T_i$ at each time is similarly repeated (step st230). The attitude matrixes $N_i$ at all the sampling times are obtained by the repetition.

In the step st300, the product of acceleration $A_i$ at each sampling time and the attitude matrix $N_i$ at the time is obtained (step st310). The acceleration $A_i$ is data itself obtained from the sensor 4. The acceleration $A_i$ at each sampling time is converted into the acceleration of the whole coordinate system by the product. The acceleration of the centrifugal component is removed by the conversion.

In the step st400, the average value of 100 data at a data initial stage is employed as the acceleration at the address. In the selection of the 100 data, for example, an address time determined by a method to be described later is used. The 50 data immediately after the address time and the 50 data immediately before the address time can be used. The number of the averaged data is suitably set.

The waveform of the acceleration from which the acceleration of the centrifugal component and the gravitational acceleration are removed is integrated in the step st500. An integration period is set to 2.0 seconds, for example.

An error referred to as a drift error may be caused in the sensor 4. The drift error is caused by a performance change in a measuring instrument or a measuring system generated after the end of calibration. Main causes of the drift error include thermal expansion of a connecting cable in the measuring instrument, and a temperature drift of a frequency converter. The drift error can be reduced by frequently executing calibration according to a change in an ambient temperature, or keeping the ambient temperature as constant as possible. However, these measures hardly eliminate the drift error completely.

The drift error is fundamentally a low-frequency component. For this reason, when complete integration is used in the integration of the step st500, amplitude (gain) at a low frequency wave is increased. That is, in this case, the drift error is apt to be increased by the integration.

In view of suppressing the drift error, incomplete integration is used in the integration of the step st500.

Herein, the complete integration and the incomplete integration will be described.

For example, when displacement X is represented by [X=A sin($\omega t$)], the displacement X is differentiated, and a velocity V is represented by the following formula.

$$V = X' = A\,\omega\cos(\omega t)$$

That is, the amplitude (gain) is $\omega$ times by the differentiation. Therefore, conversely, the amplitude (gain) is $(1/\omega)$ times by the integration. Since $\omega = 2\pi f$ is set, the amplitude is $(\frac{1}{2}\pi f)$ times by the integration. This is usual integration, and is also referred to as the complete integration.

In the golf swing, a period required for movement between the back-swing to the downswing is about 2 seconds. Therefore, the frequency of the movement is about 0.5 Hz. Consequently, the high-frequency component equal to or greater than 0.5 Hz is preferably subjected to the complete integration. On the other hand, the increase of the amplitude by the integration in the low-frequency component less than 0.5 Hz is preferably suppressed. In this case, the drift error which is the low-frequency component can be effectively suppressed. The incomplete integration is used in order to suppress the increase of the amplitude by the integration. For example, the incomplete integration is used for the low-frequency component less than 0.5 Hz.

When the acceleration is defined as a(k); the velocity is defined as v(k); the velocity after one step is defined as v(k+1); a sampling period is defined as $\Delta t$; an increment step of the integration is defined as k; and an integration period is defined as Ti, v(k+1) is obtained by the following formula (1) in the incomplete integration:

$$v(k+1) = p \cdot v(k) + q \cdot a(k) \qquad (1),$$

wherein a(0)=v(0) is set.

In the formula (1), p is referred to as a filter coefficient, and is calculated by the following formula.

$$p = \exp(-\Delta t/Ti) = \exp(-2\pi f_i \Delta t)$$

In the formula (1), q is referred to as a filter input coefficient, and is calculated by the following formula.

$$q = (1-p) \cdot Ti = (1-p)/2\pi f_i$$

Next, a method for determining the times of the address, the top, and the impact will be described. The method is divided into three stages. An impact time is determined at the first stage. A top time is determined based on the impact time at the second stage. An address time is determined based on the top time at the third stage.

At the first stage, firstly, a temporary impact time Tt is determined (step st1000). In the step st1000, a time when the grip angular velocity ωz is the maximum in the measured data is defined as a temporary impact time.

Next, a time Tp 10 msec before the temporary impact time Tt and a time Tf 10 msec after the temporary impact time are determined (step st1010).

Next, a time Ta when the grip angular velocity ωx is the minimum between the time Tp and the time Tf is determined (step st1020). A time Tb when the acceleration Az in the z axis direction is the minimum between the time Tp and the time Tf is determined (step st1030). Next, the time Ta is compared with the time Tb, and an earlier time of the times Ta and Tb is defined as the impact time (step st1040).

Figure 17:
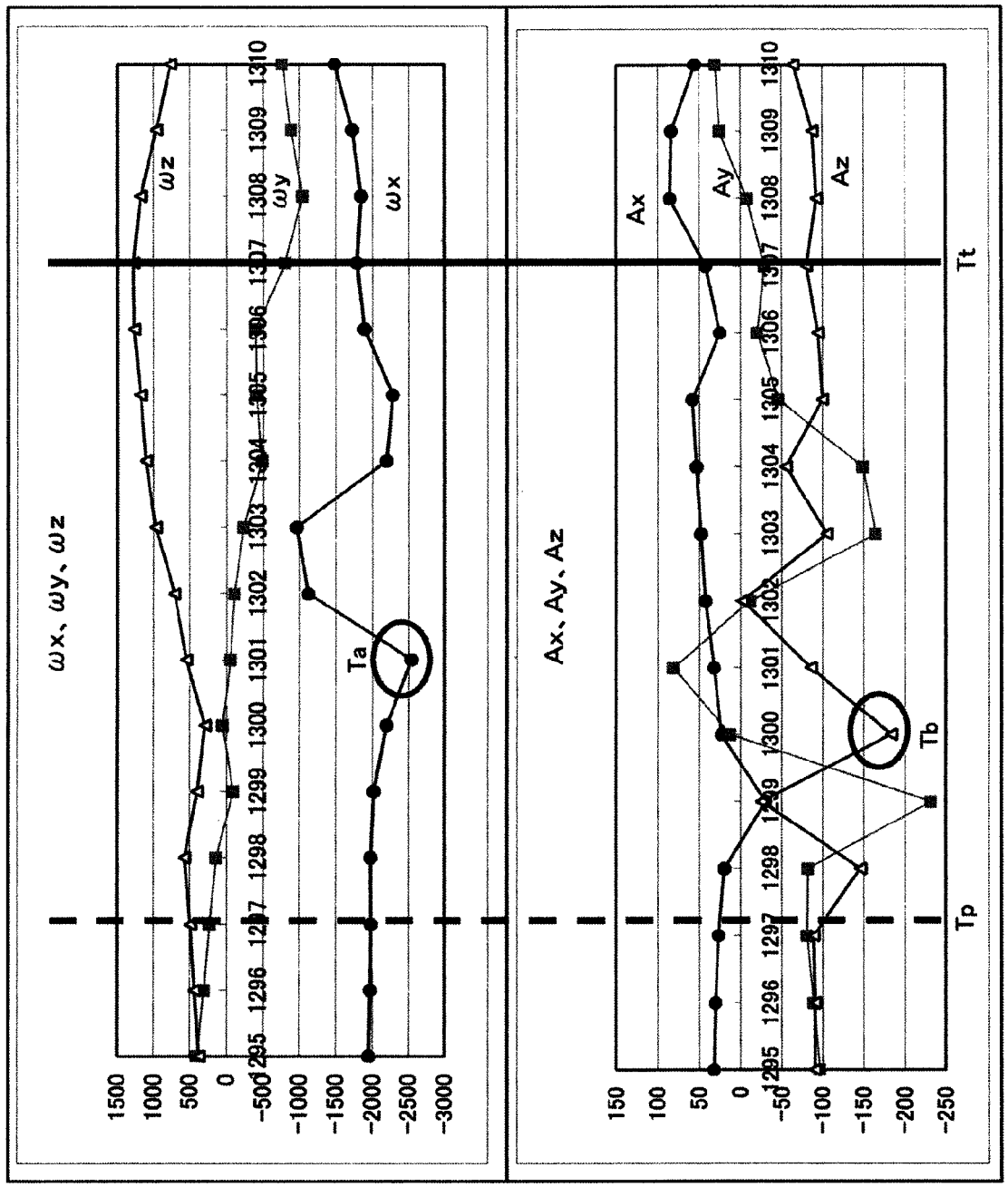
FIG. 17 is a graph showing an example of measured values by a sensor.

FIG. 17 is a graph showing an example of measurement results by the sensor 4. The upper graph of FIG. 17 shows the measurement results of the angular velocity ωx, the angular velocity ωy, and the angular velocity ωz. Round plots show the angular velocity ωx. Square plots show the angular velocity ωy. Triangular plot shows the angular velocity ωz. The lower graph of FIG. 17 shows the measurement results of the acceleration Ax, the acceleration Ay, and the acceleration Az. The round plots show the acceleration Ax. The square plots show the acceleration Ay. The triangular plots show the acceleration Az.

In FIG. 17, a thick solid line vertically extending shows the temporary impact time Tt. In FIG. 17, a thick dashed line vertically extending shows the time Tp. In FIG. 17, the time Tf is not shown. In the example of FIG. 17, the time Tb is earlier than the time Ta. Therefore, in the example, the time Tb is defined as the impact time.

The grip angular velocity ωy is used in the determination of the top time of the second stage. At the second stage, a time when the grip angular velocity ωy is zero between 0.5 second before the impact time and the impact time is defined as the top time (step st1050).

At the third stage, the address time is determined. Usually, the golfer spends a certain amount of time for the address. On the other hand, a meaning for determining the address time herein lies in the determination of the address time optimal for the swing analysis. An analysis start time suitable for the swing analysis can be determined by the determination of the address time.

Figure 18:
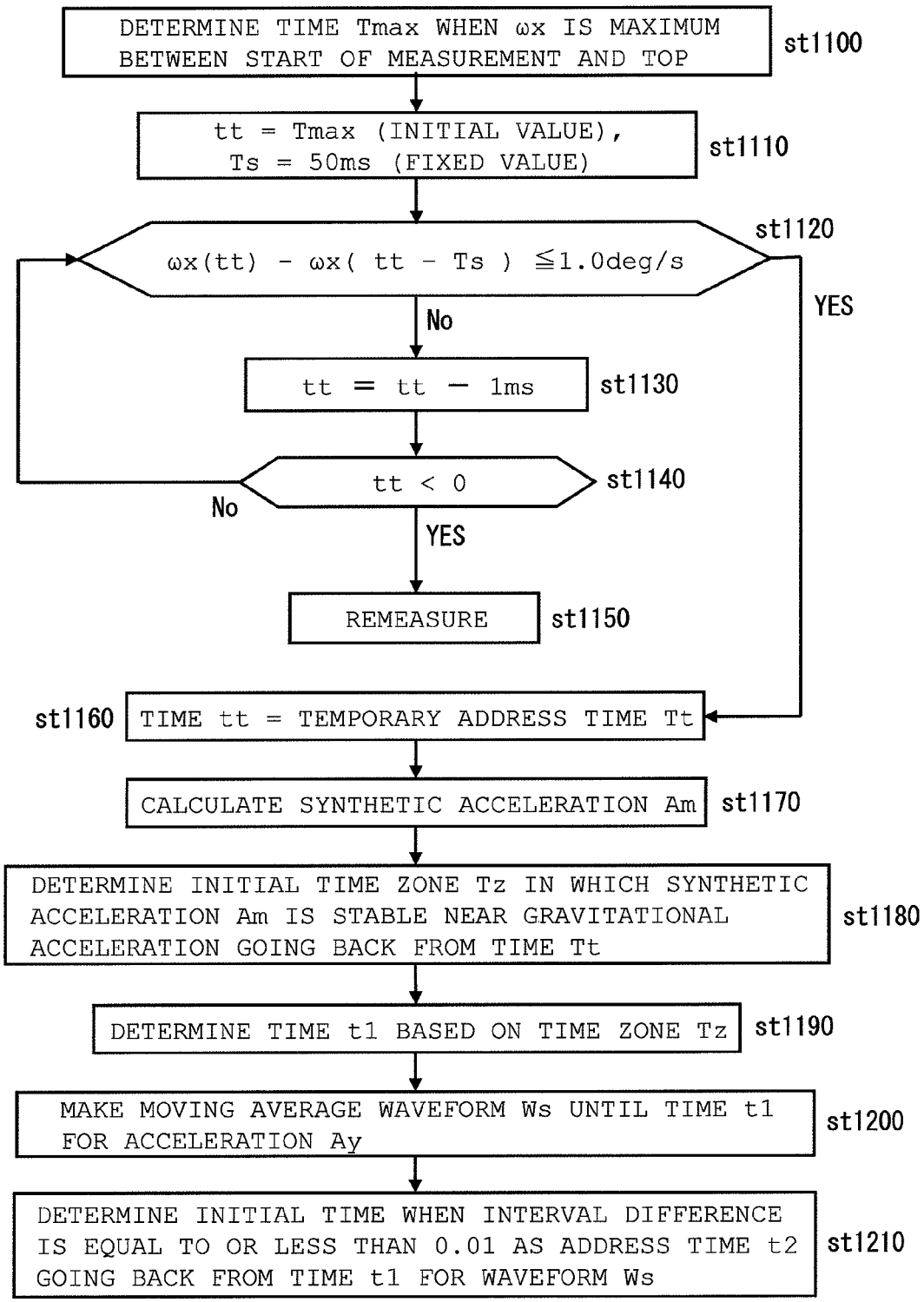
FIG. 18 is a flow chart showing an example of methods for determining an address time.

The grip angular velocity ωx is used at the third stage. FIG. 18 is a flow chart showing the third stage (address time determining method). A preferred address time determining method includes at least one selected from following steps st1100 to 1210.

In the address time determining method, a time Tmax when the angular velocity ωx is the maximum between the start of measurement and the top time is determined (step st1100).

Next, a time tt is set by using the time Tmax as an initial value (step st1110). A period Ts as a fixed value is set (step st1110). In the embodiment of FIG. 18, the period Ts is 50 ms. Values other than 50 ms may be employed.

The angular velocity ωx at the time tt is ωx(tt). The angular velocity ωx at the time (tt−Ts) is ωx(tt−Ts). It is determined whether [ωx(tt)−ωx(tt−Ts)] is equal to or less than 1.0 (deg/s) (step st1120). That is, it is determined whether the angular velocity ωx in the period Ts going back from the time tt is equal to or less than a predetermined value. Values other than 1.0 (deg/s) may be employed.

When the step st1120 is "No", the time tt is updated to a time 1 ms before (st1130). Values other than 1 ms may be employed. It is determined whether the updated time tt is smaller than 0 (step st1140). A time 0 is a measurement start time. When the time tt is smaller than 0, it is assumed that the measurement at the address time is not performed. In this case, remeasurement is performed (step st1150). When the time tt is equal to or greater than 0 in the step st1140, the processing returns to the determining step st1120.

When the step st1120 is "YES", the angular velocity ωx is small. A state where the angular velocity ωx is small is close to the address state. Therefore, the time tt in this case is determined as a temporary address time Tt (step st1160).

On the other hand, in the embodiment, the data of (not the angular velocity but) the acceleration is used. Synthetic acceleration Am is obtained by using the acceleration Ax in the direction of the x axis, the acceleration Ay in the direction of the y axis, and the acceleration. Az in the direction of the z axis (step st1170). The calculating formula of the synthetic acceleration Am is as follows.

$$Am = (Ax^2 + Ay^2 + Az^2)^{1/2}$$

Next, going back from the time Tt, an initial period zone Tz in which the synthetic acceleration Am is stable near the gravitational acceleration is determined (step st1180). Specifically, going back from the time Tt, an initial period zone in which 30 continuous data for the synthetic acceleration Am is 9.7 or greater and 10.5 or less is determined. The number of the continuous data may be other than 30. A lower limit value other than 9.7 may be employed. An upper limit value other than 10.5 may be employed.

Next, the time t1 is determined based on the period zone Tz (step st1190). For example, the time t1 may be an initial time in the period zone Tz, a last time in the period zone Tz, or a center time of the period zone Tz.

The range of 9.7 or greater and 10.5 or less is substantially close to zero if the gravitational acceleration is excluded. The acceleration other than the gravitational acceleration is close to zero in the numeric range. This is a state close to the address.

Next, a moving average waveform Ws is made for the acceleration Ay about the y axis (step st1200). Specifically, the waveform of the acceleration Ay is subjected to 50-point moving average between the time of the start of measurement and the time t1. The waveform is further subjected to 50-point moving average, to obtain a smooth waveform Ws. The number of processings of the moving average may be other than 2 times. The method of the moving average may be other than 50 points.

Next, going back from the time t1 for the waveform Ws, an initial time ti when an interval difference is equal to or less than 0.01 is determined (step st1210). A specific interval difference is a difference between the time ti and a time t (i−20). The time t(i−20) is a time going back by the amount of 20 data from the time ti. The initial time ti when the interval difference is equal to or less than 0.01 is defined as an address time t2. Threshold values other than 0.01 may be employed. The numbers of data other than 20 may be employed.

In this way, the address time t2 is determined.

When the data at the address is selected, preferably, the address time t2 is the standard. Preferably, when the data at the address is selected, a plurality of data near the address time t2 are averaged. In a preferred specific example, 50 data between the address time t2 and a time t2−50 are averaged. The time t2−50 is a time going back by the amount of 50 data from the time t2. The number other than 50 may be employed.

Next, the grip angles α, β, and γ will be described.

Figure 19:
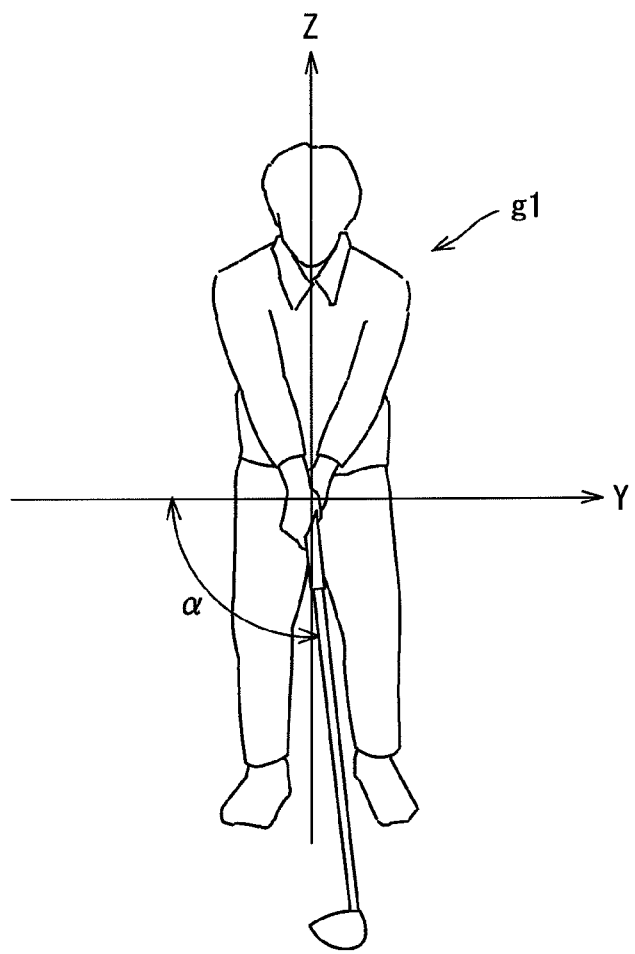
FIG. 19 shows a grip angle $\alpha$.

FIG. 19 shows the grip angle α. The grip angle α is an angle between the Y axis and a grip axis (shaft axis). The grip angle α is an angle in a two-dimensional image, as viewed from the front face. The grip angle α is equal to the grip inclination angle.

Figure 20:
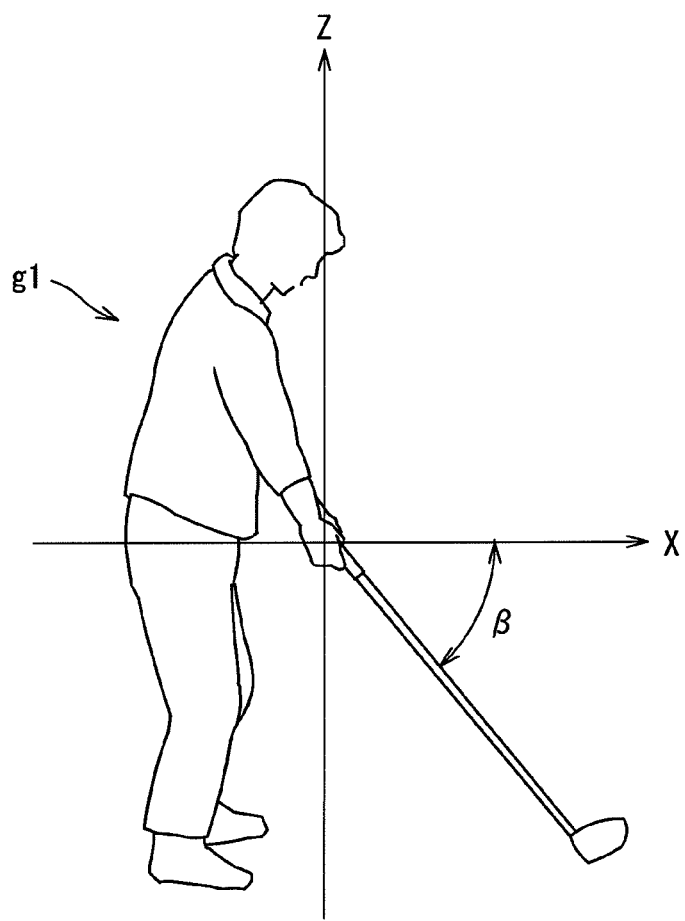
FIG. 20 shows a grip angle $\beta$.

FIG. 20 shows the grip angle β. The grip angle β is an angle between the X axis and a grip axis (shaft axis). The grip angle β is an angle in a two-dimensional image, as viewed from the back of the target direction.

Figure 21:
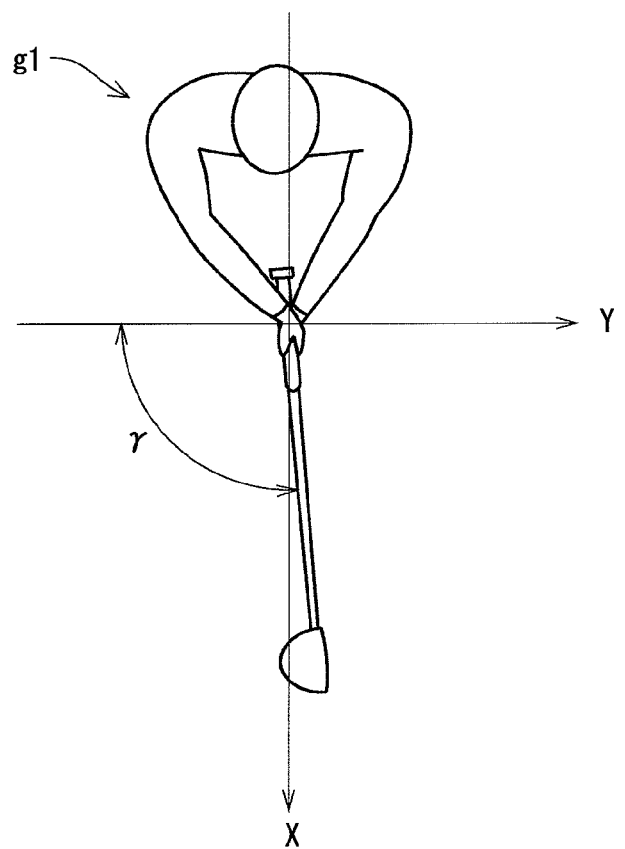
FIG. 21 shows a grip angle $\gamma$.

FIG. 21 shows the grip angle γ. The grip angle γ is an angle between the Y axis and a grip axis (shaft axis). The grip angle γ is an angle in a two-dimensional image, as viewed from above.

The grip angles α, β, and γ can be calculated based on the attitude matrix. The grip angle α can be calculated as follows by using the components f and i of the attitude matrix shown in FIG. 10.

$$\alpha = \arctan(f/-i)$$

The grip angle β can be calculated as follows by using the components c and i of the attitude matrix shown in FIG. 10.

$$\beta = \arctan(c/-i)$$

The grip angle γ can be calculated as follows by using the components c and f of the attitude matrix shown in FIG. 10.

$$\gamma = \arctan(c/f)$$

Figure 22:
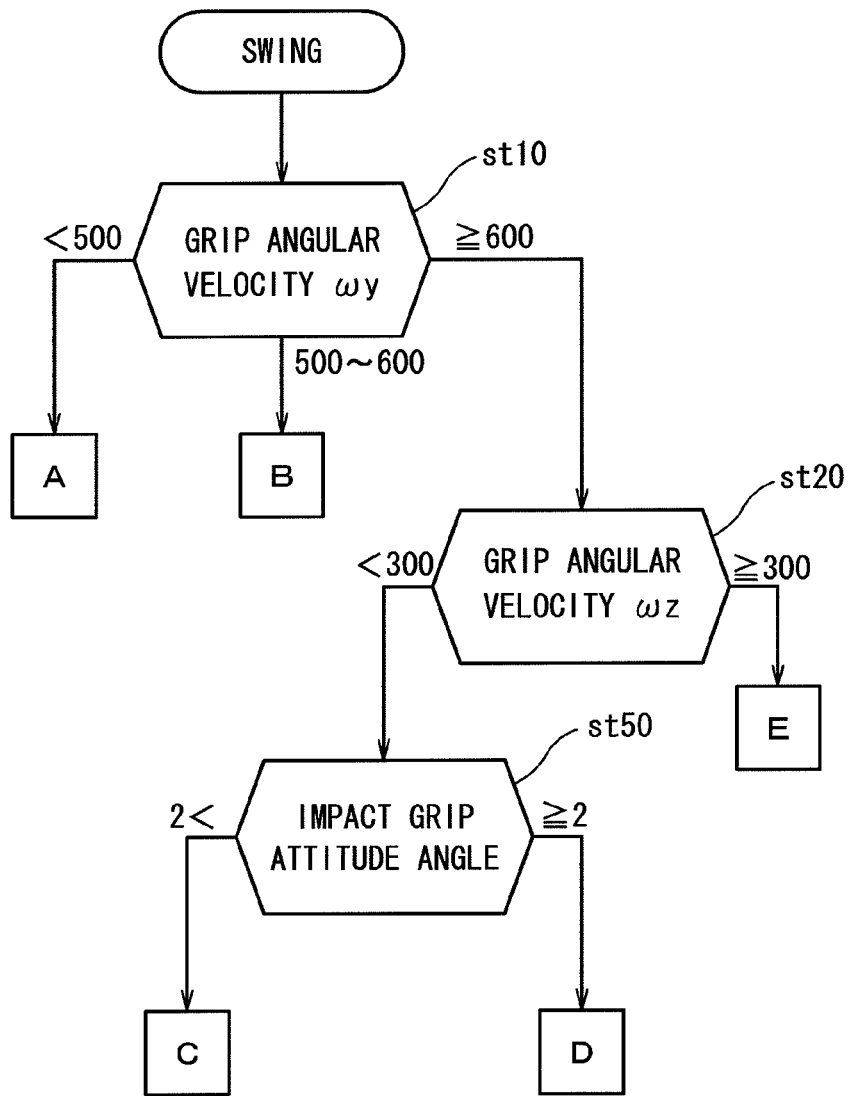
FIG. 22 is a flow chart showing another example of the steps of classifying a swing.

FIG. 22 shows a modification example of the swing classifying step st3 shown in FIGS. 8 and 9. In the example, the following items (c), (d), and (g) are used:

(c) the angular velocity ωy;
(d) the angular velocity ωz; and
(g) a grip attitude angle at the impact.

Examples of the grip attitude angle of the above item (g) includes the grip angles α, β, and γ. Preferably, the grip angle α is used.

In the flow chart of FIG. 22, the step st10 and the step st20 are the same as those of the embodiment of FIG. 8. In the embodiment, a step st50 is performed in place of the step st30. In the step st50, the grip angle α at the impact is determined. When the angle α is less than 2 (degrees), the swing is classified into the swing pattern C. When the angle α is equal to or greater than 2 (degrees), the swing is classified into the swing pattern D. Values other than 2 (degrees) may be used. That is, a threshold value can be suitably set.

The size and the weight of the sensor 4 are not limited. In view of unobstructing the swing, the sensor 4 is preferably compact and lightweight. In this view, the weight of the sensor 4 is preferably equal to or less than 10 g, and more preferably equal to or less than 6 g.

EXAMPLES

Hereinafter, the effects of the present invention will be clarified by examples. However, the present invention should not be interpreted in a limited way based on the description of the examples.

16 golfers conducted tests. All the golfers were advanced players. In all the golfers, the head speed of a driver was 42 m/s, and the weight of the driver which was normally used was equal to or greater than 300 g.

Five test clubs and a standard club were prepared. All the clubs had a common head and grip. In all the clubs, an iron number was a driver; a swing balance was set to D2; and a loft angle was set to 9.5 degrees. The total weight of the club was 307 g or greater and 323 g or less. Shafts attached to the test clubs were five kinds, that is, a shaft A, a shaft B, a shaft C, a shaft D, and a shaft E. The hardness (flex) of these shafts A to E was S. The conformity of a shaft and a swing pattern was confirmed by preliminary verification using a motion capture system. The shaft A is suitable for a golfer having a swing pattern A. The shaft B is suitable for a golfer having a swing pattern B. The shaft C is suitable for a golfer having a swing pattern C. The shaft D is suitable for a golfer having a swing pattern D. The shaft E is suitable for a golfer having a swing pattern E.

A sensor was attached to the standard club as in FIG. 2. The swing was classified based on the flow chart of FIG. 8 using the standard club. The suitable shaft was determined by classifying the swing.

Next, the suitable shaft and two shafts having a specification comparatively close to that of the suitable shaft were selected. These three shafts were compared. For example, in the case of a tester X, the result of classifying the swing was the swing pattern B, and the suitable shaft was the shaft B. The shafts A and C had a specification comparatively close to that of the shaft B. Consequently, the tester X compared the three shafts A, B, and C, and selected the best shaft. The standard of the selection included a flight distance, hitting directivity, and easiness to swing. When the best shaft was the shaft B, the case was a correct answer. When the shaft A or C was selected as the best shaft, the case was an incorrect answer.

The results of the test were as follows. 11 golfers of the 16 golfers had the correct answer for the flight distance. That is, the correct answer rate for the flight distance was 69%. On the other hand, two golfers had the incorrect answer, and three golfers had no significant difference. The existence or non-existence of the significant difference was determined at 10% of a significant level.

11 golfers of the 16 golfers had the correct answer for the hitting directivity. That is, the correct answer rate for the hitting directivity was 69%. On the other hand, three golfers had the incorrect answer, and two golfers had no significant difference. The existence or non-existence of the significant difference was determined at 10% of a significant level.

15 golfers of the 16 golfers had the correct answer for the easiness to swing. That is, the correct answer rate for the easiness to swing was 94%. On the other hand, one golfer had the incorrect answer, and 0 golfer had no significant difference. The existence or non-existence of the significant difference was determined at 10% of a significant level.

These correct answer rates are high. Advantages of the present invention are apparent.

The present invention can be applied to the analysis of the golf swing. The present invention can be applied to the fitting of the golf club or the shaft. The present invention can be applied to the development of the golf club, the golf shaft, and the golf ball. The present invention can be utilized at stores such as a golf shop.

The description hereinabove is merely for an illustrative example, and various modifications can be made in the scope not to depart from the principles of the present invention.

What is claimed is:

1. A swing analysis method comprising the steps of:
    measuring a swing of a golf club to which a sensor capable of measuring accelerations in directions of three axes and angular velocities or angles about the three axes is attached;
    obtaining an index for classifying the swing based on a measuring result of the sensor; and
    classifying the swing based on the index,
    wherein the index comprises the following item (a) or (b):
    (a) a grip angular velocity at least at one time during a downswing; and
    (b) a grip velocity at least at one time during the downswing.

2. The swing analysis method according to claim 1, further comprising the step of:
    determining times of an address, a top, and an impact,
    wherein the address is a moment of start of the swing, the impact is a moment when a head of the golf club collides with a golf ball, and the top is a moment when the head of the golf club is at a top of the swing before the impact.

3. The swing analysis method according to claim 1, wherein the index comprises at least two selected from the following items (c), (d), and (e):
    (c) a grip angular velocity in a toe-down direction;
    (d) a grip angular velocity about a shaft axis; and
    (e) a grip velocity in a direction toward a golfer.

4. The swing analysis method according to claim 3, wherein the index comprises the items (c), (d), and (e).

5. The swing analysis method according to claim 1, wherein the index comprises at least two selected from the following items (c), (d), and (f):
    (c) a grip angular velocity in a toe-down direction;
    (d) a grip angular velocity about a shaft axis; and
    (f) a dynamic loft angle of a head.

6. The swing analysis method according to claim 5, wherein the index comprises the items (c), (d), and (f).

7. The swing analysis method according to claim 1, wherein the index comprises at least two selected from the following items (c), (d), and (g):
    (c) a grip angular velocity in a toe-down direction;
    (d) a grip angular velocity about a shaft axis; and
    (g) a grip attitude angle at an impact.

8. The swing analysis method according to claim 7, wherein the index comprises the items (c), (d), and (g).

9. A method for fitting a golf club using the swing analysis method according to claim 1, wherein a recommended shaft is defined for each swing classification.

10. The swing analysis method according to claim 1, wherein the index comprises the item (b),
    an attitude matrix is used in the calculation of the grip velocity,
    acceleration of a centrifugal component and gravitational acceleration are removed in the calculation of the grip velocity, and thereafter the acceleration is integrated.

* * * * *